United States Patent
Buelow (10) Patent No.: US 10,054,357 B2
(45) Date of Patent: Aug. 21, 2018

(54) PURITY MONITOR

(71) Applicant: Raytheon Company, Waltham, MA (US)

(72) Inventor: Paul L. Buelow, Tucson, AZ (US)

(73) Assignee: RAYTHEON COMPANY, Waltham, MA (US)

(*) Notice: Subject to any disclaimer, the term of this patent is extended or adjusted under 35 U.S.C. 154(b) by 132 days.

(21) Appl. No.: 15/291,712

(22) Filed: Oct. 12, 2016

(65) Prior Publication Data

US 2018/0142937 A1   May 24, 2018

(51) Int. Cl.
| | |
|---|---|
| *F25D 19/00* | (2006.01) |
| *G01N 5/04* | (2006.01) |
| *F25B 21/02* | (2006.01) |
| *F25B 9/02* | (2006.01) |
| *F41G 7/22* | (2006.01) |

(52) U.S. Cl.
CPC ............... *F25D 19/00* (2013.01); *F25B 9/02* (2013.01); *F25B 21/02* (2013.01); *G01N 5/04* (2013.01); *F41G 7/2253* (2013.01); *F41G 7/2293* (2013.01)

(58) Field of Classification Search
CPC ... F25D 19/00; F25B 9/02; F25B 1/02; G01N 5/04; F41G 7/2253; F41G 7/2293
See application file for complete search history.

(56) References Cited

U.S. PATENT DOCUMENTS

| | | | | |
|---|---|---|---|---|
| 3,459,033 A | * | 8/1969 | Stuart | G01N 33/0016 73/28.03 |
| 3,863,495 A | * | 2/1975 | Schulz | G01N 5/04 73/61.52 |
| 5,369,033 A | * | 11/1994 | Di Milia | G01N 5/04 422/73 |
| 5,918,258 A | | 6/1999 | Bowers | |
| 6,122,954 A | | 9/2000 | Bowers | |
| 6,363,773 B1 | | 4/2002 | Bowers | |

OTHER PUBLICATIONS

QCM Research, [online]; [retrieved on Oct. 12, 2016], retrieved from the Internet URL: http://www.qcmresearch.com ; Nov. 2014, Digital, 1 page.
INFOCON, [online]; [retrieved on Oct. 12, 2016], retrieved from the Internet URL: http://products.inficon.com/en-us/nav-products/Category/ProductGroup/ThinFilmDeposition?path=Products ; Dec. 2015, Digital, 5 pages.

* cited by examiner

*Primary Examiner* — Emmanuel Duke
(74) *Attorney, Agent, or Firm* — Cantor Colburn LLP (57) ABSTRACT

A purity monitor is provided. The purity monitor includes a cryo-cooler and a piezo-electric crystal microbalance that may have a matte finish. The cryo-cooler includes a nozzle and plumbing components disposed to supply a fluid having a working pressure of up to 10,000 psig to the nozzle. The nozzle provides for locating substantially all of a pressure drop of the cryo-cooler near an exit thereof. The nozzle sprays fluid onto the piezo-electric crystal microbalance and the piezo-electric crystal microbalance measures a mass of non-volatile residue (NVR) left thereon by the spraying. Respective temperatures of the fluid and the piezo-electric crystal microbalance are controllable based on a type of the NVR.

20 Claims, 6 Drawing Sheets

PURITY MONITOR

BACKGROUND

The present invention relates to purity monitoring and, more specifically, to a gas or fluid purity monitor including a cryo-cooler and a quartz crystal microbalance (QCM).

Testing sensors and missile systems have components that operate with high-pressure gases and fluids. For example, heat seeking missiles use infrared (IR) sensors to detect electromagnetic radiation from targets and to allow for target detection and most IR sensors are cooled via compressed Argon, Freon, Nitrogen, Krypton or a combination thereof. These gases are sprayed on the detectors by a cryo-cooler or cryostat. While cryostats allow for very fast cool-down times and provide the sensor with enhanced target sensitivity, they are sensitive to contamination and can easily become clogged if the delivery system is not clean.

Delivery of clean gas has thus been a challenge for many years and led to the development of testing processes. The techniques used in the past for such testing have required specially trained personnel using labor-intensive processes and even then the processes tended to result in rather coarse measurements of NVR contaminant levels.

SUMMARY

According to one embodiment of the present invention, a purity monitor is provided. The purity monitor includes a cryo-cooler and a piezo-electric crystal microbalance. The cryo-cooler includes a nozzle and plumbing components disposed to supply a fluid having a working pressure of up to 10,000 psig to the nozzle. The nozzle provides for locating substantially all of a pressure drop of the cryo-cooler near an exit thereof. The nozzle sprays fluid onto the piezo-electric crystal microbalance and the piezo-electric crystal microbalance measures a mass of non-volatile residue (NVR) left thereon by the spraying. Respective temperatures of the fluid and the piezo-electric crystal microbalance are controllable based on a type of the NVR.

According to another embodiment, a purity monitor is provided. The purity monitor includes a housing, a two-stage Joule Thomson (JT) cryo-cooler and a quartz crystal microbalance (QCM). The two-stage JT cryo-cooler is receptive of fluid and supportively coupled to the housing and includes a nozzle and plumbing components disposed to supply a fluid having a working pressure of up to 10,000 psig to the nozzle. The nozzle provides for locating substantially all of a pressure drop of the two-stage JT cryo-cooler near an exit thereof. The QCM includes a surface disposed in the housing and onto which the two-stage JT cryo-cooler sprays the fluid. The QCM measures a mass of at least one of multiple non-volatile residues (NVRs) left on the surface by the spraying. Respective temperatures of the fluid and the surface are controllable based on a type of at least one of the multiple NVRs.

According to another embodiment, a method of measuring a purity of a fluid is provided. The method includes drawing the fluid into a two-stage Joule-Thomson (JT) cryo-cooler, maintaining a pressure of the fluid within a substantial entirety of a non-exit portion the two-stage JT cryo-cooler up to 10,000 psig, spraying the fluid from an exit portion of the two-stage JT cryo-cooler onto a surface of a quartz crystal microbalance (QCM), measuring a mass of at least one of multiple non-volatile residues (NVRs) left on the surface by the spraying and controlling respective temperatures of the fluid and the surface based on a type of the at least one of the multiple NVRs.

Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The foregoing and other features, and advantages of the invention are apparent from the following detailed description taken in conjunction with the accompanying drawings in which:

DETAILED DESCRIPTION

As will be described below, a mechanism is provided for monitoring non-volatile residue (NVR) contamination in high-pressure gases. Such high-pressure gases may be drawn, for example, from coolant systems in radiation (e.g., Infrared) detection systems of heat seeking missiles or other similar applications, especially those that are sensitive to contamination levels on the order of about 10 micrograms or less than 1 part per billion. The mechanism offers comprehensive quantification of all fluid components that will condense out of the gas or fluid when it is expanded and/or cooled.

The mechanism generally operates according to the Poynting effect. While it has been common practice to regulate high-pressure gases down to low pressures for delivery to purity measurement instruments, this can be a fundamental problem when dealing with oils with low saturated vapor pressures in consideration of the Poynting effect. Indeed, for useful measurements of these oils, the instruments of the mechanism need to be and are designed to maintain highest pressures of the tested gases and fluids. Particularly, the mechanism described herein is designed to maintain working pressures up to 10,000 psig or more with all or substantially all of a pressure drop at or near a nozzle exit. Thus, oils in the tested gases and fluids will precipitate and deposit onto a quartz crystal microbalance (QCM) for direct measurement of total mass. In this way, extra pressure drops that are typical of flow controllers and pill particle filters are avoided and lags and false readings that commonly occur in purity measurement systems are eliminated.

Figure 1:
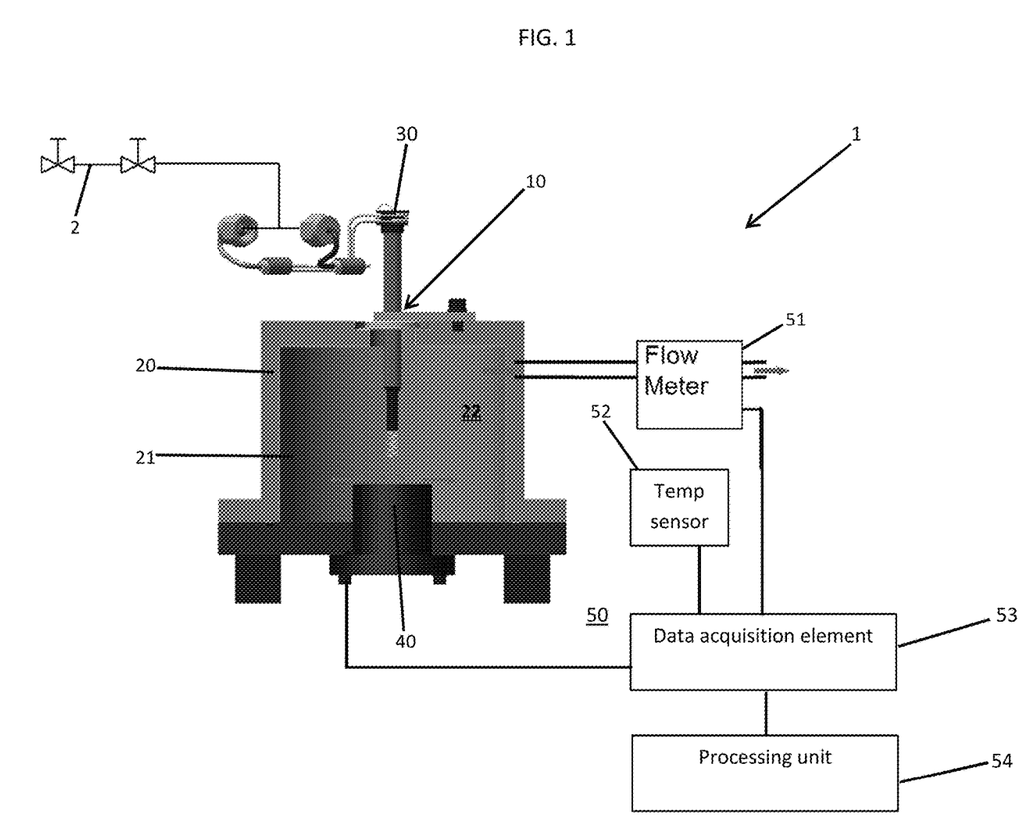
FIG. 1 is a side view of a gas or fluid test monitoring system in accordance with embodiments.
Figure 2:
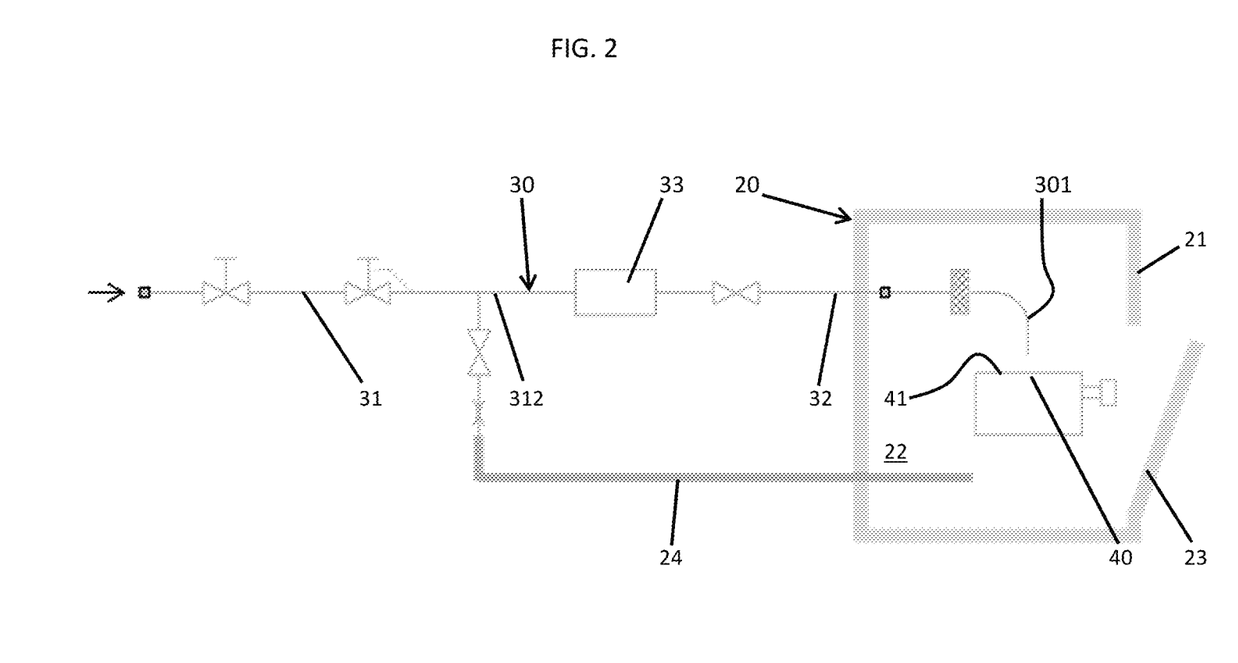
FIG. 2 is a schematic illustration of a nozzle and plumping components of the gas or fluid test monitoring system of FIG. 1.

With reference to FIG. 1 and FIG. 2, a gas or fluid test monitoring system 1 is provided and includes a gas or fluid purity monitor 10. The gas or fluid purity monitor 10 includes a housing 20, a cryo-cooler 30 and a QCM 40. The gas or fluid test monitoring system 1 includes a fluid supply source 2 that is disposed to deliver gas or fluid to the gas or fluid test monitoring system 1 for testing. The fluid supply source 2 may be a cryo-cooling system of an Infrared (IR) radiation system of a heat seeking missile or a high pressure fluid drawn from a radiation detection system. Thus, the gas or fluid test monitoring system 1 may be disposed and configured to test heat seeking missile coolant or other types of missile or non-missile coolants or high pressure fluid of radiation detection systems for purity and other characteristics. The gas or fluid test monitoring system 1 may further include a control system 50 that is configured to control various operations of the cryo-cooler 30 and the QCM 40. The control system 50 may include a flow meter 51, a temperature sensor 52 disposed to sense temperatures within the cryo-cooler 30, a data acquisition element 53 and a processing unit 54 with software installed therein to analyze the data and to control the various operations of the cryo-cooler 30 and the QCM 40. The processing unit 54 may have software or executable instructions installed therein that, when executed, execute these controls.

The housing 20 includes a housing body 21 that is formed to encompass and house components of the cryo-cooler 30 and the QCM 40 and interior 22 thereof. The housing 20 may further include a sidewall 23 that can be opened and closed so that the housed components and especially the QCM 40 can be removed and replaced. The housing 20 may also include a fitting for a purge line 24 that extends into the interior 22 from upstream components of the cryo-cooler 30.

With continued reference to FIGS. 1 and 2 and with additional reference to FIGS. 3-6, the housing 20 includes a first part 200 and a second part 201 that are secured together by fittings to define the interior 22. The interior 22 may be, but is not required to be hermetically sealed and in some embodiments may be provided at nominally atmospheric conditions. The first part 200 includes a first aperture in an axial endwall thereof and the second part 201 includes a second aperture in an axial endwall thereof as well. The cryo-cooler 30 may be supportively coupled to the first part 200 of the housing 20 such that components thereof extend through the first aperture and into the interior 22. A flanged retainer 204 may be provided to secure the cryo-cooler 30 in place relative to the first aperture. Similarly, the QCM 40 may be supportively coupled to the second part 201 of the housing 200 such that components thereof may be disposed in the interior 22.

Figure 3:
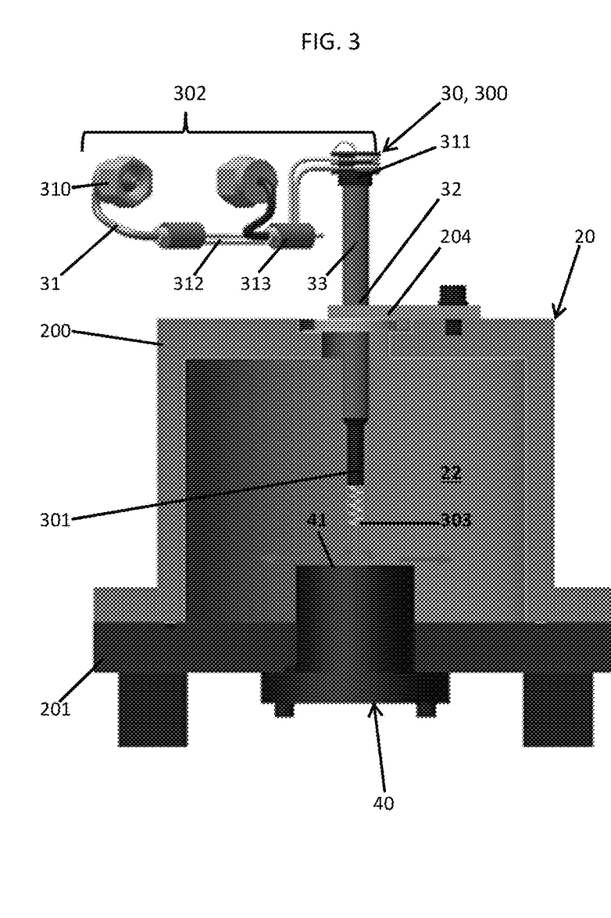
FIG. 3 is an enlarged side view of components of the gas or fluid test monitoring system of FIG. 1.

The cryo-cooler 30 may be provided, for example, as a two-stage Joule-Thomson (JT) cryo-cooler 300 that is receptive of the gas or fluid from the fluid supply source 2. The cryo-cooler 30 is supportively coupled to the housing 20 and includes a nozzle 301 and plumbing components 302. The plumbing components 302 are disposed and configured to supply the gas or fluid to the nozzle 301 with a working pressure of up to 10,000 psig or more. The nozzle 301 extends into the interior 22 of the housing 20 and is formed to define an exit 303. The nozzle 301 and the exit 303 are disposed and configured to provide for location substantially all of a total pressure drop of the cryo-cooler 30 (or the two-stage JT cryo-cooler 31) at or near the exit 303.

For purposes of clarity and brevity, the following description will relate to the case in which the cryo-cooler 30 is provided as the two-stage JT cryo-cooler 300 and in which the gas or fluid being tested is high pressure fluid (coolant or otherwise).

The cryo-cooler 30 includes a first end 31 and a second end 32 opposite the first end 31. The first end 31 includes high pressure gas fittings 310, a capture hub 311, piping 312 leading from the fittings 310 to the capture hub 311 and a filtering system 313 disposed along the piping 312. A supply of the fluid is removed or received from the fluid supply source 2 by the fittings 310 and is transmitted through the filtering system 313 along the piping 312 to the capture hub 311. The piping 312 may also be coupled to the purge line 24 whereby purge air that can be used to clean the interior 22 of the housing 20 can be pumped by the purge line 24 from the piping 312 and into the interior 22. The filtering system 313 may be provided as in-line particle filters or other suitable filters that are capable of removing particles of a given size from the supply of the fluid. The second end 32 is supportively coupled to the first part 200 of the housing 20 by the flanged retainer 204. The nozzle 301 is coupled to a distal portion of the second end 32.

By avoiding extra pressure drops typical of flow controllers and pill particle filters, the cryo-cooler 30 eliminates lag and false readings that commonly occur in purity measurement systems. The cryo-cooler 30 employs no sintered pill filters but rather uses a single screen filter with negligible pressure drop as the filtering system 313.

The cryo-cooler 30 may further include a cooler 33, which is fluidly interposed between the capture hub 311 and the second end 32. The supply of the fluid transmitted through the filtering system 313 and along the piping 312 to the capture hub 311 is subsequently transmitted through the cooler 33 to the nozzle 301, which is configured to subsequently spray or discharge the fluid outwardly. The cooler 33 may employ a supply of coolant (e.g., a second fluid), which is selected from a group of one or more coolants (see FIG. 4), to cool the fluid to a selected one of multiple and various temperature ranges prior to the spraying or the discharging.

Figure 4:
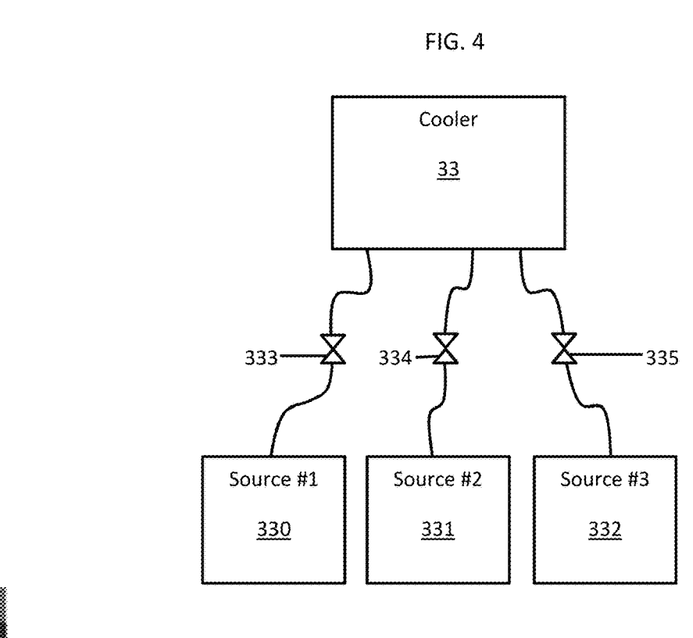
FIG. 4 is a schematic diagram of a coolant system of a cryo-cooler in accordance with embodiments.

As shown in FIG. 4, the cooler 33 may be fluidly coupled to multiple sources 330-332 of coolant and may include a plurality of valves 333-335 provided to permit each coolant to flow into and through the cooler 33 in order to provide cooling to the fluid. The valves 333-335 may be disposed in signal communication with the control system 50 or another controller including servo elements respectively associated with each of the valves 333-335.

Figure 5:
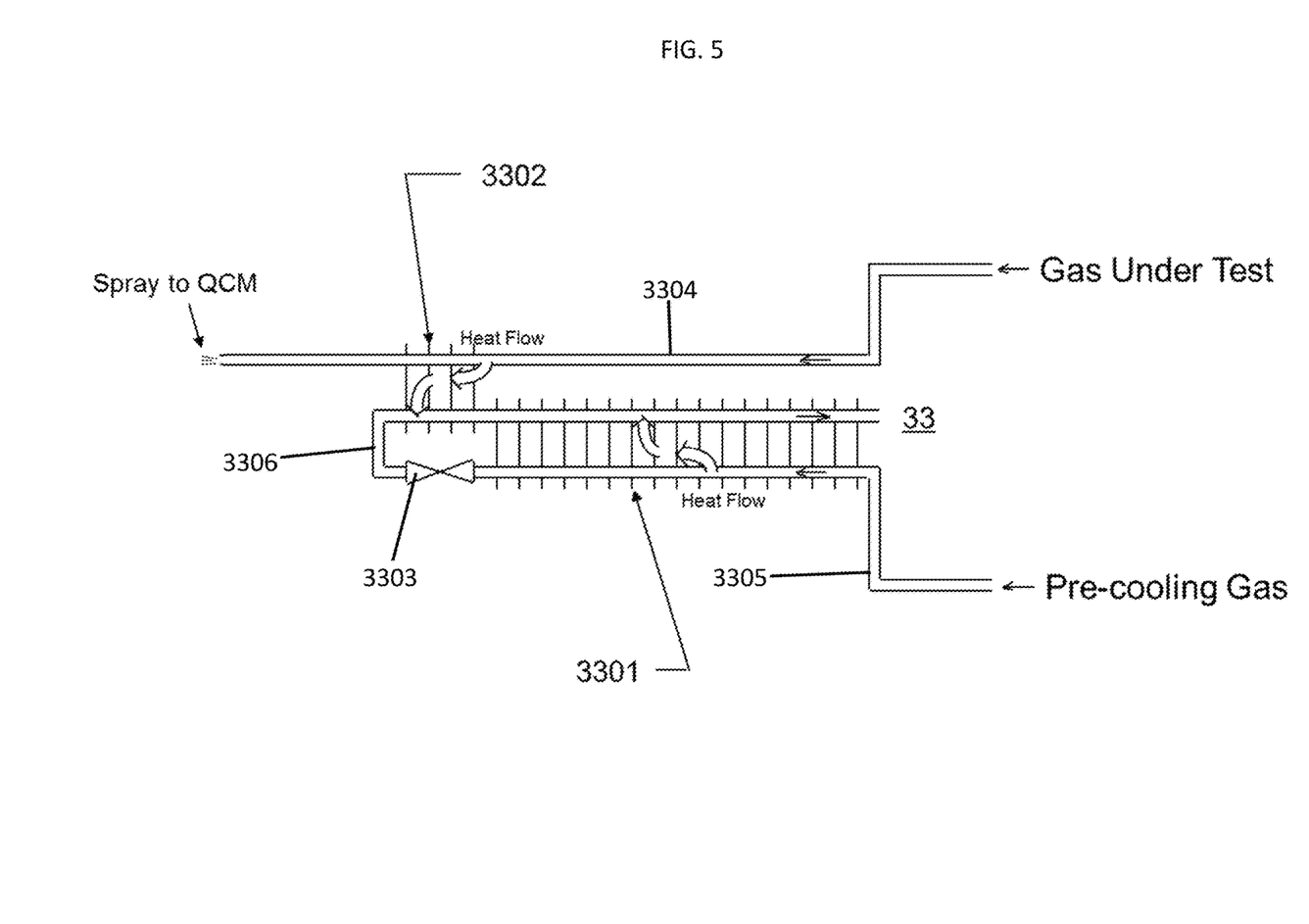
FIG. 5 is a schematic illustration of a two-stage cryo-cooler in accordance with embodiments.

As shown in FIGS. 4 and 5, the cooler 33 may include a first stage heat exchanger 3301, a second stage heat exchanger 3302 and a fluid expansion valve 3303. During operations of the cooler 33, the supply of the fluid (i.e., the gas-under-test) flows along main line 3304 to the nozzle 301 (see FIG. 3) whereupon it is sprayed or discharged onto the QCM 40. Along the main line 3304, the supply of fluid is cooled (or heated) within the second stage heat exchanger 3302. Meanwhile, coolant from any one or more of the multiple sources 330-332 (i.e., the pre-cooling gas), which may be gaseous or liquid nitrogen, for example, flows through first coolant line 3305 to the fluid expansion valve 3303 and from the fluid expansion valve 3303 through the second coolant line 3306 from which it is exhausted. In so doing, the coolant in the first coolant line 3305 gives up heat to the coolant in the second coolant line 3306 within the first stage heat exchanger 3301 and is expanded and substantially cooled by the fluid expansion valve 3303. Due to this substantial cooling resulting from such expansion, the coolant draws heat from the supply of the fluid in the second stage heat exchanger 3302 and still remains colder than the coolant in the first coolant line 3305. Thus, as the coolant flows along the second coolant line 3306, it is still capable of drawing heat from the coolant in the first coolant line 3305.

Figure 6:
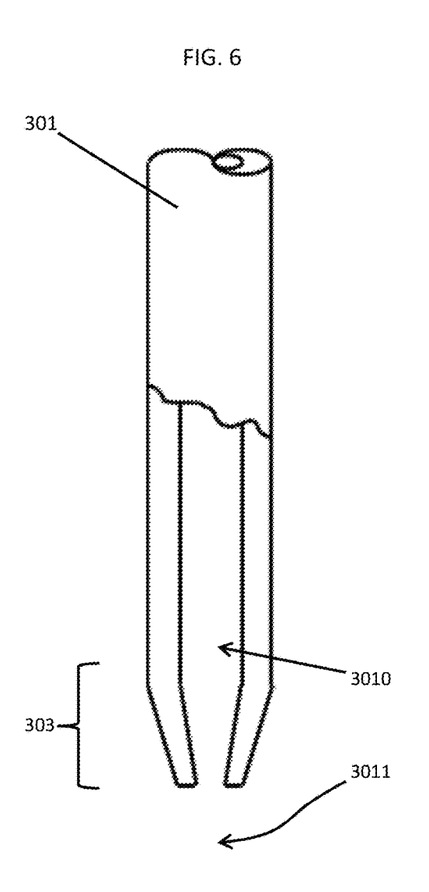
FIG. 6 is a side view of a nozzle of the gas or fluid test monitoring system of FIG. 1.

The cryo-cooler 30 and the nozzle 301 are both generally designed to sustain the fluid at working pressures of up to 10,000 psig or more. The nozzle 301 is further formed to provide for all or substantially all of the pressure drop through the system to occur at or near its exit 303 to avoid trapping oils therein. Thus, as shown in FIG. 6, the nozzle 301 extends away from the second end 32 and toward the surface 41 of the QCM 40. The nozzle 301 includes a tubular element that is formed to define the exit 303 to include a nozzle orifice 3010 and a vena contracta 3011. The vena contracta 3011 is provided by a tapering of the tubular element downstream from the nozzle orifice 3010.

The QCM 40 may be provided as a piezo-electric QCM 40 and includes a surface 41 that is disposed in the interior 22 of the housing 20. Fluid sprayed or otherwise discharged from the exit 303 of the nozzle 301 impinges upon this surface 41. Once such fluid impingement occurs, the fluid flows outwardly from its contact point. The fluid then experiences a substantial pressure drop during which one or more NVRs precipitate out of the fluid and adhere to the surface 41. The QCM 40 is thereafter configured to measure or be used to measure a mass or, more generally, a quantity, of at least one or more of multiple NVRs left on the surface 41 by the spraying or discharging of the nozzle 301.

Figure 7:
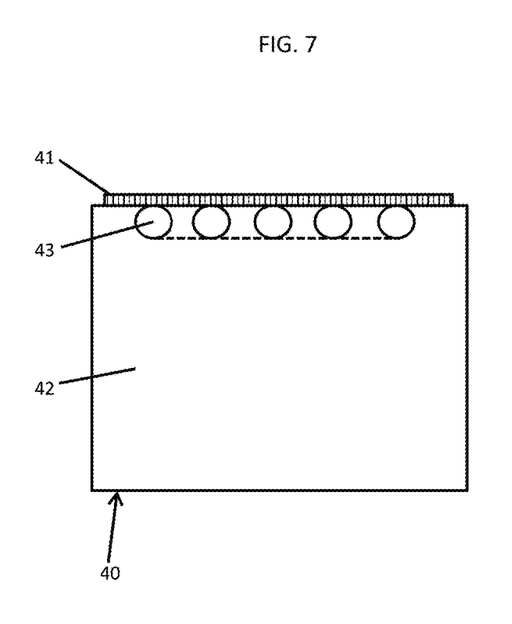
FIG. 7 is a side view of a quartz crystal microbalance and a heating/cooling element in accordance with embodiments.
Figures 8, 9, 10:
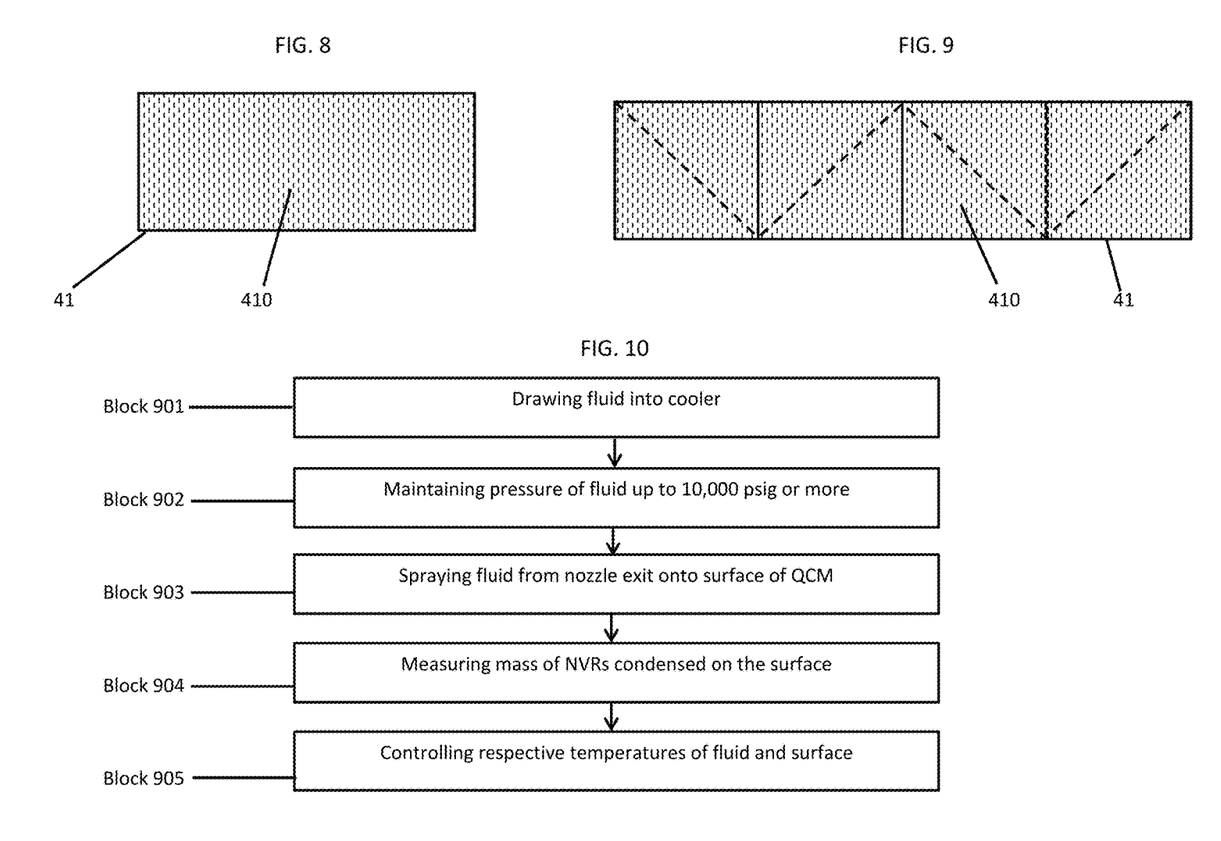
FIG. 8 is a plan view of a quartz crystal microbalance in accordance with embodiments.
FIG. 9 is a plan view of a quartz crystal microbalance in accordance with further embodiments.
FIG. 10 is a flow diagram illustrating a method of measuring a purity of a fluid in accordance with embodiments.

As shown in FIG. 3 and with additional reference to FIGS. 7-9, the QCM 40 includes a body 42 that is provided with an active thermal element 43 on which the surface 41 is operably disposed. The active thermal element 43 may be provided as one or both of a resistive heating element and a thermo-electric cooler. The surface 41 is operably disposed on the body 42 such that the surface 41 can be acted upon by electrical and oscillating components in the body 42 as well as the active thermal element 43. The surface 41 may be formed of quartz crystal or another material that experiences piezo-electric effects and may be about 7-10 mils thick or less.

As a general matter, a QCM is often configured to measure a mass variation per unit area by measuring a change in a frequency of a quartz crystal resonator when a rigid mass is applied thereto. The QCM 40 described herein, however, serves to measure the mass of NVRs that condense out of the fluid and onto the surface 41 upon the spraying or the discharging by the cryo-cooler 30. The QCM 40 can be used under vacuum conditions, in gas phase conditions and/or in liquid environments with capabilities to make high precision frequency and dissipation factor measurements.

In accordance with embodiments, the nozzle 301 and the surface 41 may be arranged in line along a gravitational direction within the interior 22 of the housing 20. Thus, the nozzle 301 may be disposed to spray or discharge the fluid downwardly onto the surface 41 in a normal direction with respect to a plane thereof.

As shown in FIG. 8, the surface 41 faces the nozzle 301 and has a matte finish 410. The matte finish 410 is formed by micro-abrading the surface 41 and leads to microscopic abrasions in the surface 41 that serve to slow down and partially constrain the NVRs that condense out of the fluid as the fluid impinges on the surface 41 and flows outwardly. In accordance with further embodiments and, as shown in FIG. 9, a grain of the matte finish 410 may be oriented to be substantially transverse relative to a radial dimension of the surface 41 extending from a central region thereof to a periphery thereof. As such, as the fluid flows outwardly from the point at which it impinges on the surface 41, the fluid generally encounters matte finish abrasions that extend across its predominant flow direction.

The surface 41 of FIG. 9 may be formed, for example, by an abrading of the surface 41 in a radial or angular pattern or assembled. Such assembly can be conducted by segmenting an elongate crystal having a crosswise matte finish into short segments and then segmenting each of those short segments into triangular cutouts. Those triangular cutouts can then be adhered together about a common focal point to form a polygonal shaped (e.g., hexagonal or octagonal) crystal whose matte finish abrasions generally form a polygonal shape that follows the overall shape of the crystal.

It is to be understood that since QCMs are often designed to respond to rigid material attached to their surfaces, they have not been previously used to measure a level of liquid oil as done here. This is partially due to the fact that it has not been clear that one could configured the various elements described herein in such a way as to result in a large enough sample being contained and thus detectable or quantifiable on the surface 41. The matte finish 410 addresses this issue as condensed oils can reside within the texture of the matte finish 410 and thus behave as though rigidly attached.

In accordance with embodiments, the gas or fluid test monitoring system 1 can be used to generate reliable readings of a given mass of NVRs on the surface 41. For example, with a spray distance of 0.15" and a matte finish 410 for the surface 41, a spray of argon gas with a light oil contaminant at near room temperature provides for linear readings up to about 15 micrograms. Above that level, the gain of the gas or fluid test monitoring system 1 rolls off and becomes insensitive above 60 micrograms. This is consistent with the capability of the nozzle 301 to contain or hold approximately 8-10 micrograms of fluid at any one time during the spraying or the discharging (a burn-in period may be required before the nozzle 301 will expel NVRs at a steady rate).

With the configurations described above, the QCM 40 may be configured to measure a mass or quantity of at least one of multiple non-volatile residues NVRs left on the surface 41 by the spraying or discharging of the fluid by the nozzle 301. Any one or more of these multiple NVRs may be carried by the fluid and would be a candidate for identification and quantity determination by the gas or fluid test monitoring system 1. To this end, the gas or fluid test monitoring system 1 itself or an operator of the gas or fluid test monitoring system 1 will determine temperature ranges at which each NVR would be expected to condense out of the fluid. Using this determination, the cooler 33 of the cryo-cooler 30 and the active thermal element 42 of the QCM 40 are cooperatively, jointly or separately operable such that respective temperatures of the fluid and the surface 41 are controllable by the control system 50. In accordance with embodiments, the respective temperatures of the fluid and the surface 41 are controllable based on a type of the at least one of the multiple NVRs.

In accordance with further aspects and, with reference to FIG. 10, a method of measuring a purity of a gas or fluid is provided. The method includes drawing the fluid into a two-stage Joule-Thomson (JT) cryo-cooler (block 901), maintaining a pressure of the fluid within a substantial entirety of a non-exit portion the two-stage JT cryo-cooler up to 10,000 psig (block 902), spraying the fluid from an exit portion of the two-stage JT cryo-cooler onto a surface of a QCM (block 903), measuring a mass of at least one of multiple non-volatile residues (NVRs) left on the surface by the spraying (block 904) and controlling respective temperatures of the fluid and the surface based on a type of the at least one of the multiple NVRs (block 905).

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts and equivalents of all means or step plus function elements in the claims below are intended to include any structure, material or act for performing the function in combination with other claimed elements as claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiments were chosen and described in order to best explain the principles of the invention and the practical application, and to enable others of ordinary skill in the art to understand the invention for various embodiments with various modifications as are suited to the particular use contemplated.

While embodiments have been described, it will be understood that those skilled in the art, both now and in the future, may make various improvements and enhancements which fall within the scope of the claims which follow. These claims should be construed to maintain the proper protection for the invention first described.

What is claimed is:

1. A purity monitor, comprising:
   a cryo-cooler comprising a nozzle and plumbing components disposed to supply a fluid having a working pressure of up to 10,000 psig to the nozzle,
   the nozzle being configured to provide for locating substantially all of a pressure drop of the cryo-cooler near an exit thereof; and
   a piezo-electric crystal microbalance onto which the nozzle sprays fluid and which is configured to measure a mass of non-volatile residue (NVR) left thereon by the spraying,
   respective temperatures of the fluid and the piezo-electric crystal microbalance being controllable based on a type of the NVR.

2. The purity monitor according to claim 1, wherein the fluid comprises high pressure fluid drawn from a radiation detection system.

3. The purity monitor according to claim 1, wherein the cryo-cooler comprises:
   a first end receptive of the fluid;
   a second end coupled to the nozzle;
   a cooler configured to lower a temperature of the fluid prior to spraying; and
   a filtering system fluid interposed between the first end and the cooler.

4. The purity monitor according to claim 1, wherein the exit of the nozzle comprises a nozzle orifice and a vena contracta downstream from the nozzle orifice.

5. The purity monitor according to claim 1, wherein the piezo-electric crystal microbalance comprises a quartz crystal microbalance (QCM).

6. The purity monitor according to claim 5, wherein the QCM comprises:
   a quartz crystal; and
   an active thermal element on which the quartz crystal is disposable.

7. The purity monitor according to claim 6, wherein the quartz crystal is about 7-10 mils thick or less and the active thermal element comprises at least one or both of a resistive heater and a thermoelectric cooler.

8. The purity monitor according to claim 7, wherein a surface of the quartz crystal facing the nozzle has a matte finish.

9. The purity monitor according to claim 8, wherein a grain of the matte finish is transverse relative to a radial dimension of the surface extending from a central region thereof to a periphery thereof.

10. The purity monitor according to claim 1, wherein the temperature controller controls the respective temperatures for multiple types of NVRs.

11. A purity monitor, comprising:
    a housing;
    a two-stage Joule-Thomson (JT) cryo-cooler receptive of fluid and supportively coupled to the housing, the two-stage JT cryo-cooler comprising a nozzle and plumbing components disposed to supply a fluid having a working pressure of up to 10,000 psig to the nozzle, the nozzle being configured to provide for locating substantially all of a pressure drop of the two-stage JT cryo-cooler near an exit thereof; and
    a quartz crystal microbalance (QCM) comprising a surface disposed in the housing and onto which the two-stage JT cryo-cooler sprays the fluid, the QCM being configured to measure a mass of at least one of multiple non-volatile residues (NVRs) left on the surface by the spraying,
    respective temperatures of the fluid and the surface being controllable based on a type of the at least one of the multiple NVRs.

12. The purity monitor according to claim 11, wherein the fluid comprises high pressure fluid drawn from a radiation detection system.

13. The purity monitor according to claim 11, wherein the two-stage JT cryo-cooler comprises:
    a first end receptive of the fluid;
    a second end coupled to the nozzle and supportively disposed in the housing;
    a cooler configured to lower a temperature of the fluid prior to spraying; and
    a filtering system fluid interposed between the first end and the cooler.

14. The purity monitor according to claim 11, wherein the exit of the nozzle comprises a nozzle orifice and a vena contracta downstream from the nozzle orifice.

15. The purity monitor according to claim 11, wherein the QCM comprises:
    a quartz crystal that is about 7-10 mils thick or less; and
    an active thermal element comprising at least one or both of a resistive heater and a thermoelectric cooler on which the quartz crystal is disposable.

16. The purity monitor according to claim 15, wherein a surface of the quartz crystal facing the nozzle has a matte finish with a grain oriented transversely relative to a radial dimension of the surface extending from a central region thereof to a periphery thereof.

17. A method of measuring a purity of a fluid, the method comprising:
 drawing the fluid into a two-stage Joule-Thomson (JT) cryo-cooler;
 maintaining a pressure of the fluid within a substantial entirety of a non-exit portion the two-stage JT cryo-cooler up to 10,000 psig;
 spraying the fluid from an exit portion of the two-stage JT cryo-cooler onto a surface of a quartz crystal microbalance (QCM);

measuring a mass of at least one of multiple non-volatile residues (NVRs) left on the surface by the spraying; and controlling respective temperatures of the fluid and the surface based on a type of the at least one of the multiple NVRs.

18. The method according to claim 17, further comprising:

selecting the type of the at least one of the multiple NVRs for measurement;

determining a temperature at which the type of the at least one of the multiple NVRs selected for measurement condenses out of the fluid; and controlling the respective temperatures of the fluid and the surface in accordance with the determined temperature.

19. The method according to claim 17, wherein:

the controlling of the temperature of the fluid comprises selecting a coolant from a group of coolants to cool the fluid to a selected one of various temperatures, and the controlling of the temperature of the surface comprises heating or cooling the surface.

20. The method according to claim 17, further comprising:

matte finishing the surface; and orienting a matte finish grain transversely relative to a radial dimension of the surface extending from a central region thereof to a periphery thereof.

* * * * *